(12) United States Patent
Prasad

(10) Patent No.: US 12,329,764 B2
(45) Date of Patent: *Jun. 17, 2025

(54) COMPOSITION FOR PROMOTING NORMAL URINARY FUNCTION

(71) Applicant: Vidya Herbs, Inc., Fullerton, CA (US)

(72) Inventor: Kodimule Shyam Prasad, Bangalore (IN)

(73) Assignee: Vidya Herbs, Inc., Red Bank, NJ (US)

( * ) Notice: Subject to any disclaimer, the term of this patent is extended or adjusted under 35 U.S.C. 154(b) by 377 days.

This patent is subject to a terminal disclaimer.

(21) Appl. No.: 18/083,502

(22) Filed: Dec. 17, 2022

(65) Prior Publication Data
US 2023/0226078 A1 Jul. 20, 2023

Related U.S. Application Data

(63) Continuation of application No. 17/186,600, filed on Feb. 26, 2021, now Pat. No. 11,559,532, which is a continuation of application No. 16/525,176, filed on Jul. 29, 2019, now Pat. No. 10,960,014.

(60) Provisional application No. 62/711,834, filed on Jul. 30, 2018.

(51) Int. Cl.
*A61K 31/575* (2006.01)
*A61K 9/00* (2006.01)
*A61K 36/889* (2006.01)
*A61P 13/08* (2006.01)

(52) U.S. Cl.
CPC .......... *A61K 31/575* (2013.01); *A61K 9/0056* (2013.01); *A61K 9/0095* (2013.01); *A61K 36/889* (2013.01); *A61P 13/08* (2018.01)

(58) Field of Classification Search
CPC .................................................... A61K 31/575
See application file for complete search history.

(56) References Cited

U.S. PATENT DOCUMENTS 10,960,014 B2  3/2021  Prasad
11,559,532 B2  1/2023  Prasad
2005/0260285 A1  11/2005  DiMateeo-Leggio

OTHER PUBLICATIONS

Strum, "Beta-Sitosterol" Life Extension Magazine, Jun. 2005, pp. 1-8.

*Primary Examiner* — Sahar Javanmard
(74) *Attorney, Agent, or Firm* — TMB Law; Timothy M. Brown

(57) ABSTRACT

The invention provides a composition and method for treating prostate disorders. The composition can be formulated to provide a saw palmetto oil having about 3% w/w β-sitosterol.

12 Claims, 13 Drawing Sheets

COMPOSITION FOR PROMOTING NORMAL URINARY FUNCTION

CROSS-REFERENCE TO RELATED APPLICATIONS

This application is a continuation of U.S. application Ser. No. 17/186,600 filed Feb. 26, 2021, which is a continuation of U.S. application Ser. No. 16/525,176 filed Jul. 29, 2019, which claims the benefit of U.S. Provisional Application No. 62/711,834 filed Jul. 30, 2018. The entire contents of these applications are incorporated herein by reference for all purposes.

FIELD OF INVENTION

The invention generally relates to compositions and methods for the treatment of prostate disorders. More particularly, the invention relates to a composition of β-sitosterol and method of its use in treating benign prostate hyperplasia and prostatitis.

BACKGROUND OF THE INVENTION

Benign prostate hyperplasia (BPH) is a common prostate disease affecting older men. It is a major cause of lower urinary tract symptoms which deteriorate quality of life (Gupta et al. 2015). BPH pathogenesis has been associated with factors such as genetic predisposition, hormonal imbalance, imbalance in cell proliferation and death, and inflammation (Pawlicki et al. 2004). The current therapy for BPH involves administration of 5-α reductase inhibitors, phosphodiesterase-5 inhibitors, and laser therapy. 5-α reductase inhibitors effectively reduce the conversion of testosterone to dihydrotestosterone (DHT), and hence decrease the BPH progression. While these treatments can improve the quality of life, some patients feel worse due to the side effects of the treatment. For example, Finasteride™ is a 5-α reductase inhibitor that can effectively alleviate the complications of BPH (Nickel et al. 2011). However, Finasteride™ is associated with undesirable side effects such as erectile dysfunction, increased risk of impotency, and ejaculation disorder. Moreover, natural treatments for BPH, such as saw palmetto oil, lack the degree of efficacy needed to effectively treat BPH.

What is needed in the art therefore is a treatment for BPH that lacks the side effects of small molecule BPH therapy and provides greater efficacy than available natural treatments for BPH.

SUMMARY OF THE INVENTION

It is an object of the invention to provide a composition and method for treating a prostate disorder that is free of the side effects of small molecule prostate disorder therapies and has greater efficacy than natural prostate disorder treatments that are currently available.

In some aspects, the composition comprises 3% w/w β-sitosterol.

In a further aspect of the invention, the composition comprises saw palmetto oil having 3% w/w β-sitosterol.

In some aspects of the invention, the prostate disorder is BPH, prostatitis, or a combination thereof.

In some aspects, the invention treats one or more prostate disorder symptoms selected from enlarged prostate, increased prostate weight, inflammation, inhibited apoptosis of prostate tissue, and prostate growth.

The present disclosure demonstrates that the inventive composition surprisingly possesses superior in vivo efficacy compared to saw palmetto oil. Study subjects showed a significant increase in prostate growth following sub-cutaneous administration of testosterone, while a 21-day treatment with the inventive composition appreciably improved hyperplastic conditions as evident from parameters such as prostate weight, prostate weight to body weight ratio, growth inhibition of prostate, and serum testosterone levels. The inventive composition effectively suppressed prostatic inflammation and strongly induced apoptosis in the prostate tissue of the study subjects.

DETAILED DESCRIPTION OF THE INVENTION

Figure 1:
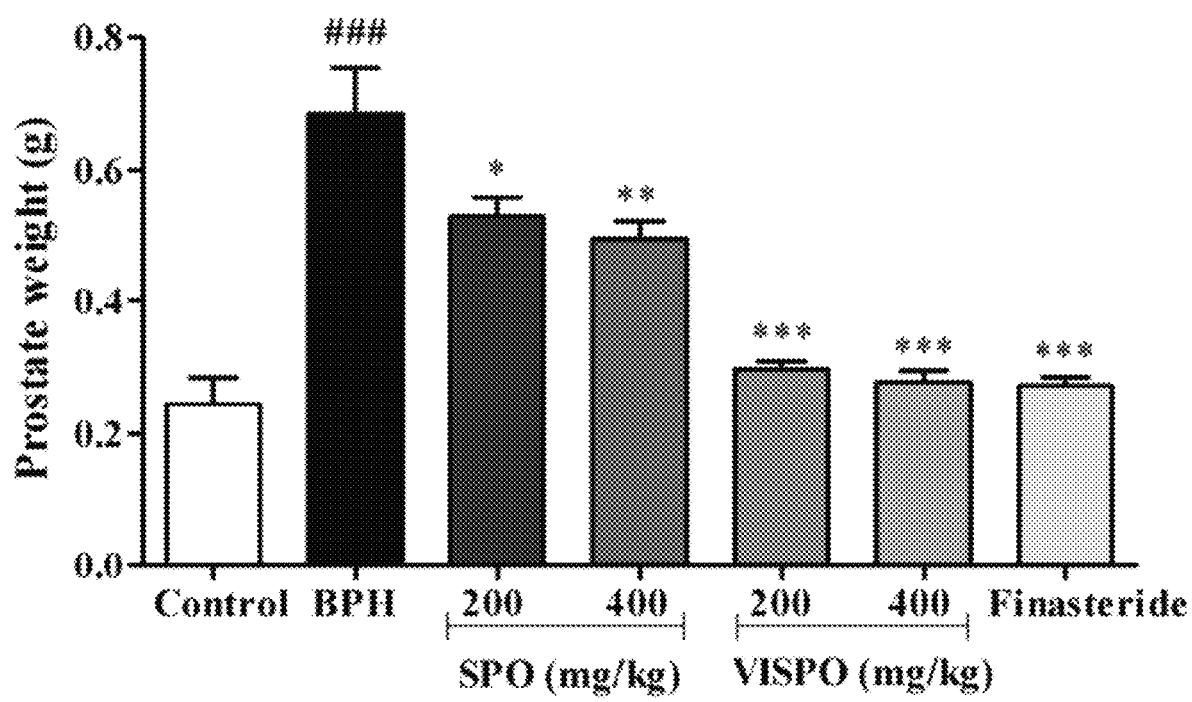
FIG. 1 shows a comparison of the effect of saw palmetto oil (SPO) and an embodiment of the inventive composition on prostate weight and prostate to body weight ratio.

The invention provides a composition and method of treating disorders of the prostate without producing the side effects associated with contemporary prostate disorder treatments and with greater efficacy than present-day natural therapies.

The invention provides a composition for treating prostate disorders. In one non-limiting embodiment of the invention, the composition comprises about 3% w/w β-sitosterol. As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% from the referenced quantity, level, value, number, frequency, percentage, dimension, size, amount, weight or length. In some embodiments of the invention, the composition comprises a saw palmetto oil having about 3% w/w β-sitosterol. The saw palmetto oil for formulating the composition can be obtained from, for example, *Serenoa repens*. The composition can be formulated by combining saw palmetto oil with β-sitosterol to provide a saw palmetto oil composition having about 3% w/w β-sitosterol.

As demonstrated by the accompanying examples, the inventor surprisingly discovered that formulating saw palmetto oil with about 3% w/w β-sitosterol provides greater efficacy in treating the symptoms and inflammatory mechanisms associated with prostate disorders compared to a saw palmetto oil that lacks the formulation of the inventive composition.

In some embodiments of the invention, the composition further comprises one or more substances selected from a vitamin, mineral, extract, amino acid, protein, carbohydrate, lipid, fatty acid, excipient, pharmaceutically acceptable carrier, bulking agent, binding agent, caffeine, flavouring, sweetener, and preservative. Excipients for use with the composition can be selected on the basis of their compatibility with the composition's active ingredients and the properties of the desired dosage form. Suitable, excipients include, but are not limited to, binders, fillers, flow aids/glidents, disintegrants, lubricants, stabilizers, surfactants, and the like. Suitable excipients include, but are not limited to, those disclosed in the following publications, the disclosures of which are incorporated herein by reference in their entirety for all purposes: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The composition can be formulated, and administered as, a food, food supplement, beverage, or nutritional supplement.

In at least one aspect of the invention, the composition is provided and/or manufactured in bulk. The composition can be provided in bulk for the manufacture of foods, nutritional supplements, nutraceuticals, dietary supplements and/or food supplements for the treatment of pain. Bulk quantities of the composition can be packaged, stored and/or distributed in drums, bags, boxes, containers and the like. Such containers can be configured to prevent or inhibit the oxidation of the active ingredients of the composition.

In at least one embodiment, the invention provides a method of treating a prostate disorder in a patient in need thereof. As used herein, the terms "treat," "treating," "treatment," and the like, can refer to the clinical intervention of a disease or condition in an attempt to alter, alleviate, ameliorate, prevent, inhibit or reverse the progression or symptoms of the disease or condition.

The method can be practiced by administering, to a patient in need of treatment for a prostate disorder, an effective amount of the composition disclosed herein. The prostate disorder can be BPH, prostatic inflammation, or a combination thereof. Administering the composition can treat one or more symptoms of the prostate disorder, including, without limitation, frequent or urgent need to urinate, increased frequency of urination, difficulty starting urination, weak urine stream, urine stream that stops and starts, dribbling at the end of urination, involuntary urination, painful urination, inability to completely empty the bladder, urinary tract infection, inability to urinate, and blood in the urine. In at least one aspect of the invention, administering the composition treats the underlying causes of the symptoms of the prostate disorder. For example, administering the composition can inhibit or reverse prostatic inflammation, increase apoptosis of prostate tissue, decrease serum testosterone, reduce prostate size, inhibit increases in prostate size, or combinations thereof.

The composition can be administered systemically. Suitable administration routes for the composition include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parentera, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. The composition can be administered by irrigation, drip, infusion, or topically by a dressing, patch, or bandage that is in contact with the composition.

The present invention is explained in detail by the following examples. Example 1 describes BPH induction and dosage of the composition and Finasteride™ to experimental rats. Example 2 illustrates the effect of the composition and Finasteride™ on prostate growth in rats. Example 3 describes the influence of treatments on serum testosterone levels in BPH rats. Example 4 illustrates the effect of the composition and Finasteride™ on the histology of prostate tissue. Example 5 relates to the effect of the composition on the expression of inflammatory markers in the prostate tissue of testosterone induced BPH rats. Example 6 describes the influence of the composition on the regulation of apoptosis in the prostate tissue of rats. Example 7 describes the binding mode of β-sitosterol with IkB and NF-kB proteins through in silico docking. Example 8 illustrates molecular interaction of β-sitosterol with the BH-3 binding groove of antiapoptotic Bcl-2 protein.

Example 1

Induction of Benign Prostatic Hyperplasia in Rats

Animals

Forty-two male Wistar rats (10 week old) were purchased from Biogen, Bangalore, India (CPCSEA Reg. No. 971/bc/06). The animals were housed in accordance with the CPCSEA (Committee for the Purpose of Control and Supervision of Experiments on Animals) guidelines. After a one-week acclimatization period the animals were housed in rooms maintained at 22±2° C. and 30-70% humidity. Water and standard pellet diet were given ad libitum. The animals were randomly divided into seven groups, each group consisting of six animals with less than 20% mean body weight range.

BPH Induction and Dosage

BPH was induced in rats using testosterone 5 mg/kg subcutaneously and a simultaneous treatment with different doses of saw palmetto preparations viz. Saw palmetto oil (SPO) and the inventive composition (200 and 400 mg/kg b.w.) or Finasteride (1 mg/kg b.w.) p.o., was followed for 21 days (Table 1). The inventive composition (VISPO) was a composition of saw palmetto oil having 3% β-sitosterol. At the end of the treatment period, blood was collected prior to the necropsy. Animals were sacrificed by overdose of anesthetics. The vital parameters such as prostate weight, prostate weight to body weight ratio, growth inhibition of prostate, serum testosterone level, expression of inflammatory and apoptotic proteins in prostate tissue were evaluated.

TABLE 1

Experimental design (n = 6 in each group)

| Groups | Treatment mg/kg b.w. |
|---|---|
| Control | 0.1% CMC in saline |
| BPH | Testosterone 5 mg/kg b.w. + 0.1% CMC in saline |
| SPO | Testosterone 5 mg/kg b.w. + 200 mg/kg p.o. |
|  | Testosterone 5 mg/kg b.w. + 400 mg/kg p.o. |
| VISPO | Testosterone 5 mg/kg b.w. + 200 mg/kg p.o. |
|  | Testosterone 5 mg/kg b.w. + 400 mg/kg p.o. |
| Finasteride | Testosterone 5 mg/kg b.w. + Finasteride 1 mg/kg b.w. |

Example 2

Effect on Prostate Growth

Following a 21-day treatment with the saw palmetto oil preparations and/or Finasteride, prostate tissues were excised, rinsed and weighed immediately after removal. The PW/BW ratio was calculated using the following equation: PW/BW ratio=(Prostate weight of each animal from experimental group/Body weight of each animal from experimental group)×1000. The percentage of growth inhibition was calculated as follows: 100−[(treated group−control group)/(BPH group−control group)]×100.

The mean prostate weight of animals in the BPH group was significantly increased as compared to the normal rats ($p<0.001$) indicating testosterone induced BPH in rats. The prostate weights were reduced considerably in the Finasteride and VISPO treated groups ($p<0.001$). There was a dose dependent decrease of prostate weight in treated animals (FIG. 1). The prostate weight in BPH group was 2.83 fold higher than control group of rats (Table 2). The treated groups exhibited appreciable reduction in prostate weight. There was a reduction of 1.28 and 1.38 fold in prostate weight of 200 and 400 mg/kg SPO treated rats respectively. Interestingly, groups with VISPO showed a highly significant decrease in the prostate weight compared to the BPH group ($p<0.001$). At the 400 mg/kg dose, VISPO effectively reduced the prostate weight by 2.43 fold which was comparable to the Finasteride treatment (2.51 fold). Further, the PW/BW ratio in BPH group was significantly increased as compared to the control group ($p<0.001$). Administration of SPO preparations reduced the PW/BW ratio significantly in a dose dependent manner (FIG. 1B). The data were highly significant in VISPO treatment as compared to BPH group ($p<0.001$). The percentage growth inhibition of prostate was 90.9% at 400 mg/kg in the VISPO treated group.

TABLE 2

Prostate growth in BPH model rats

| Group | Prostate weight (g) | Inhibition of growth (%) |
|---|---|---|
| Control | 0.24 ± 0.04 | — |
| BPH | 0.68 ± 0.07### | — |
| SPO (200 mg/kg) | 0.53 ± 0.03* | 34.09 |
| SPO (400 mg/kg) | 0.49 ± 0.03** | 43.18 |
| VISPO (200 mg/kg) | 0.29 ± 0.01*** | 88.63 |
| VISPO (400 mg/kg) | 0.28 ± 0.02*** | 90.9 |
| Finasteride (1 mg/kg) | 0.27 ± 0.01*** | 93.18 |

The data were represented as mean ± SEM (n = 6).
$p < 0.001$ vs. control group;
*$p < 0.05$,
**$p < 0.01$ and
***$p < 0.001$ vs. BPH group. Growth inhibition = 100 − ((treated group-control group)/(BPH group-control group) × 100)
SPO: Saw palmetto oil;
VISPO: saw palmetto oil with 3% β-sitosterol

Example 3

Effect on Serum Testosterone Levels

Blood samples were collected at the end of experiment and coagulated at room temperature for 20 min. Serum was separated by centrifuging at 3000 g, 4° C. Serum samples were analyzed for testosterone levels using commercial ELISA kit (582701; Cayman Chemical Co., Ann Arbor, MI, USA) following manufacturer's protocol.

Figure 2:
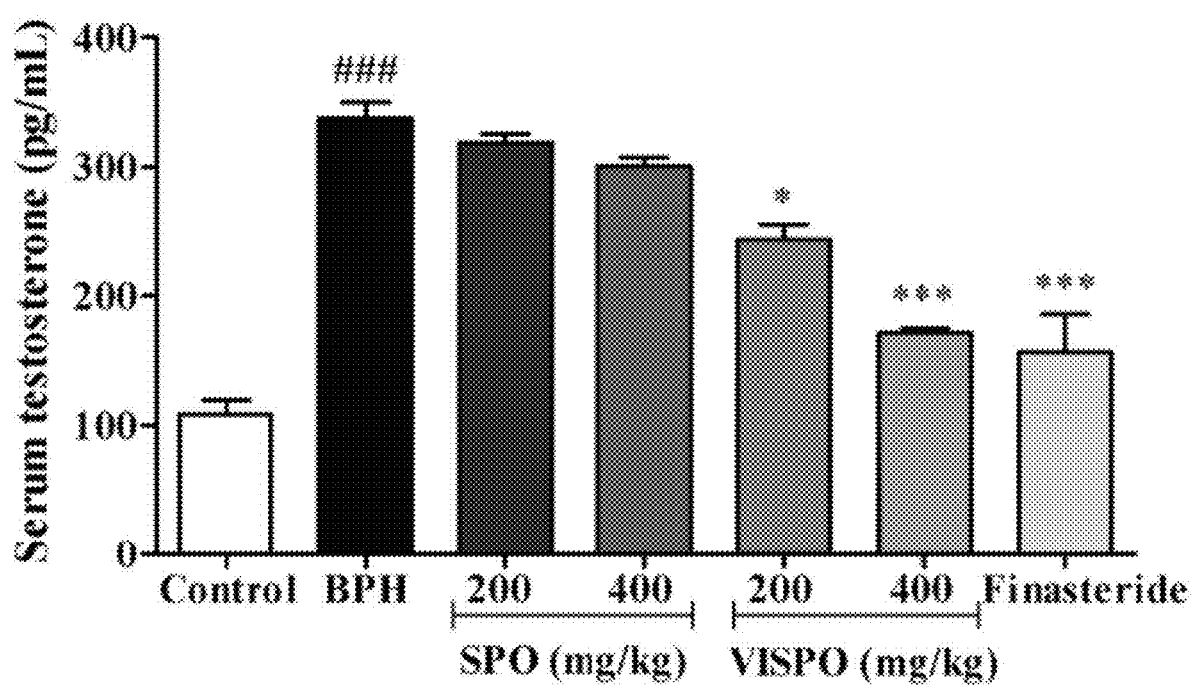
FIG. 2 shows a comparison of the effect of saw palmetto oil (SPO) and an embodiment of the inventive composition on serum testosterone levels.

The serum testosterone level was significantly higher in the BPH group (337.5±12.15 pg/mL) as compared to control rats (108.6±14.92 pg/mL). As shown in FIG. 2, the level of testosterone was decreased in the treatment groups. The values were highly significant in the 400 mg/kg VISPO treated group and comparable to Finasteride ($p<0.001$).

Example 4

Effect on Hyperplastic Patterns in Prostate Tissue of BPH Rats

The prostate tissue samples were fixed in 4% formalin, dehydrated with a graded alcohol series, embedded in paraffin, and then cut into 4 μm thickness. The sections were stained with hematoxylin and eosin (H&E, Sigma-Aldrich, St. Louis, MO, USA). The images were captured using a microscope (Leica, Germany).

Figure 3A:
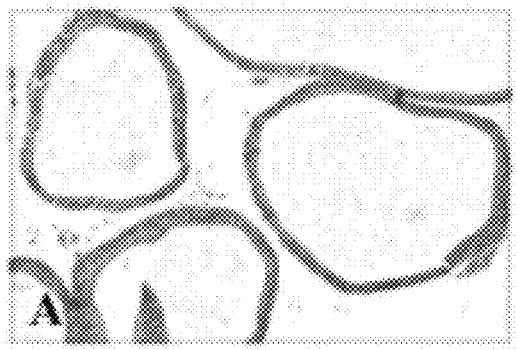
FIGS. 3A-3G show a comparison of the effect of saw palmetto oil (SPO) and an embodiment of the inventive composition on the histology of prostate tissue.
Figure 3B:
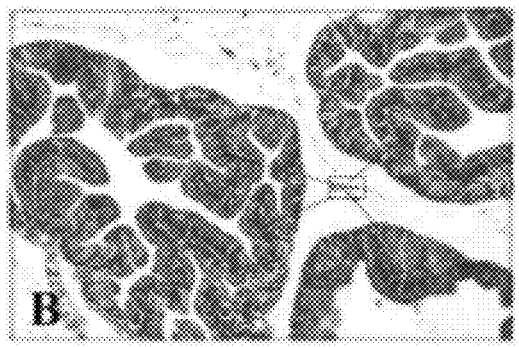
Figure 3C:
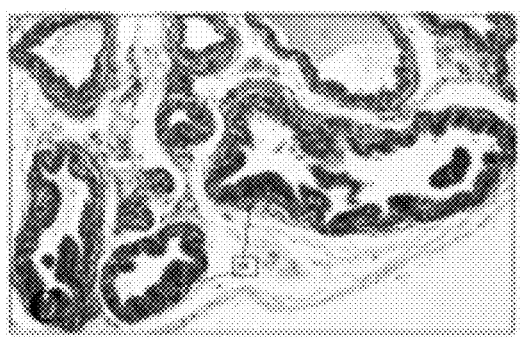
Figure 3D:
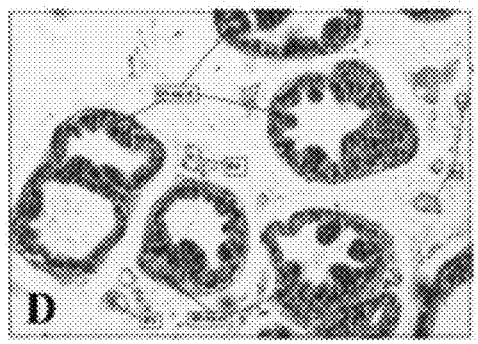
Figure 3E:
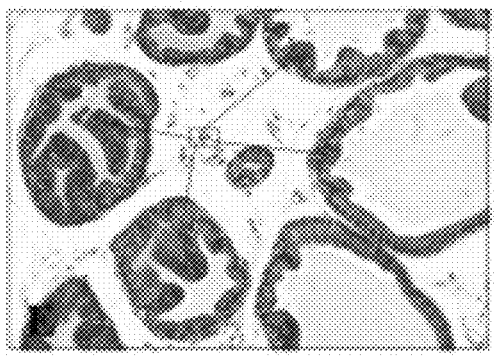
Figure 3F:
Figure 3G:
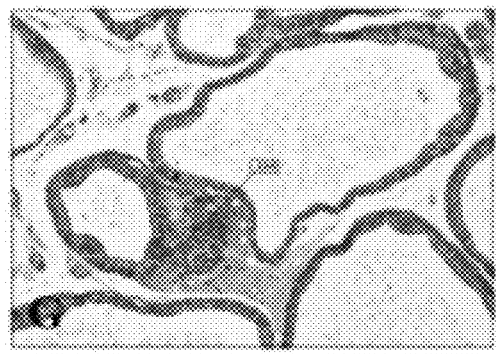

Histological examination of prostate tissue revealed that the testosterone treatment induced glandular hyperplasia with decreased glandular luminal area compared to the control animals (FIG. 3B). SPO (200 and 400 mg/kg) and 200 mg/kg VISPO treatment groups exhibited moderate suppression of hyperplastic patterns (FIGS. 3C-E). 400 mg/kg VISPO treatment markedly restored the cellular architecture in BPH rats (FIG. 3F). The epithelial cell thickness was reduced and the luminal area increased considerably. The finasteride group also showed near normal prostatic glands with mild focal inflammation (FIG. 3G).

Example 5

Effect on Expression of Inflammatory Markers in Prostate Tissue

The prostatic tissue from each animal was homogenized in lysis buffer and incubated for 20 minutes to induce cell lysis. Tissue extracts were centrifuged at 12000 rpm for 20 minutes and the supernatants were transferred to clean tubes. Aliquots of protein samples (30 μg) were resolved on 8-15% sodium dodecyl sulphate-polyacrylamide gel electrophoresis gels and transferred on to a nitrocellulose membrane. The membranes were incubated for 1 hr with blocking solution and subsequently incubated with 1:500 dilution of primary antibodies, anti-NF-kB and anti-COX-2 overnight at 4° C.

The membranes were washed three times with 0.1% Tween 20 in TBS followed by incubation with Horseradish peroxidase conjugated goat IgG antibody (1:4000 dilution) for 1 h at room temperature. Detection was performed on ImageQuant™ LAS 500 (GE Healthcare Life Sciences). Densitometry analyses of the results were made using Image J software (version 1.46, National Institutes of Health, Bethesda, Maryland). β-actin was used as a loading control.

Figure 4:
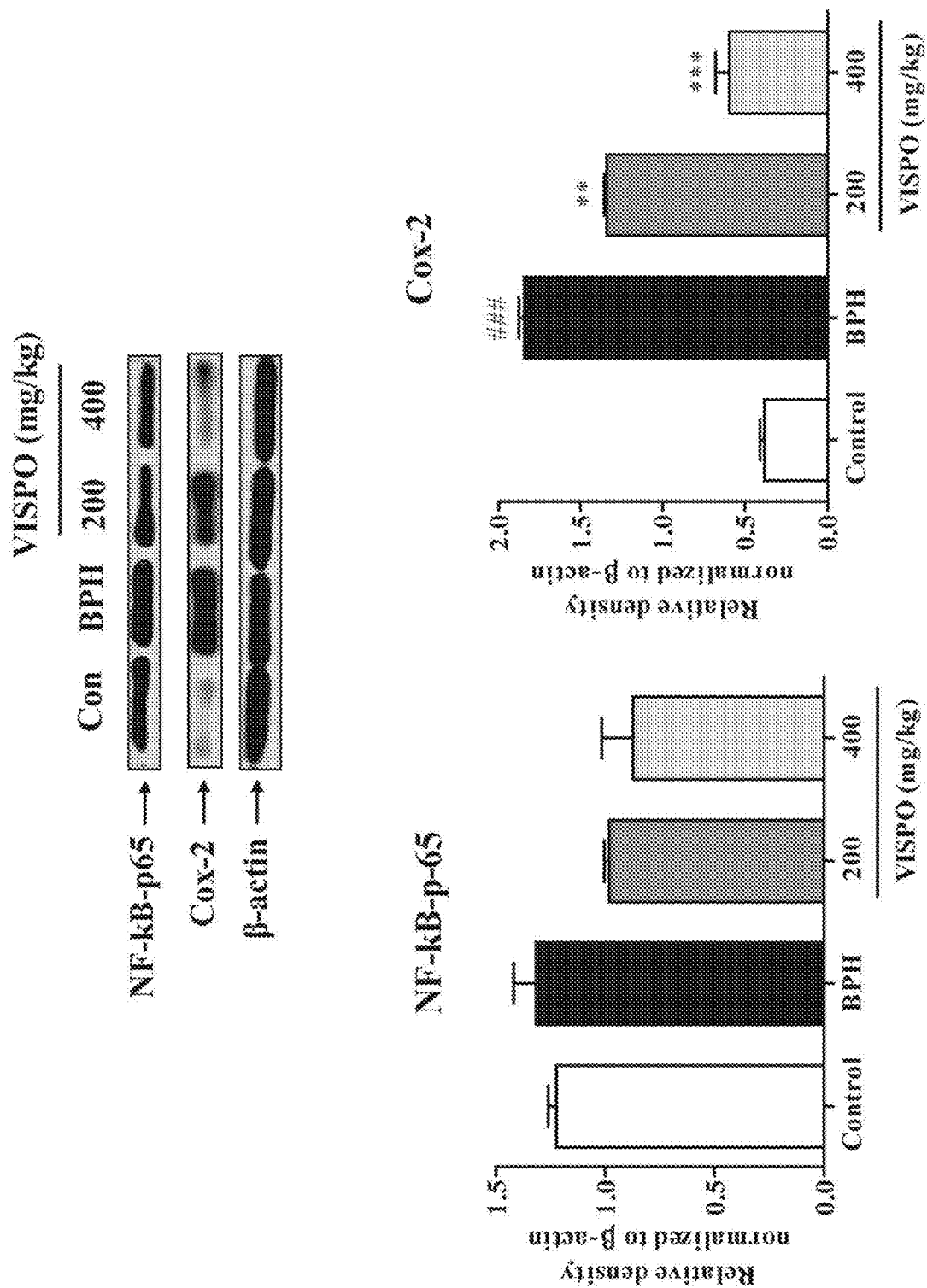
FIG. 4 shows the effect an embodiment of the inventive composition on the expression of inflammatory markers.

Testosterone treatment markedly increased the expression of NF-kB (p<0.05) and COX-2 (p<0.001) in prostate tissue of BPH rats as compared to the control group. However, treatment with VISPO significantly down-regulated the expression of these proteins in a dose dependent manner (FIG. 4).

Example 6

Effect on the Induction of Apoptosis in Prostate Tissue of BPH Rats

The prostate tissue lysates were subjected to western blotting as described in Example 5 for the analysis of phosphorylated Akt (Ser473), caspase-9, Bcl-2 and Bax protein expression in the VISPO treated BPH rats.

Figure 5A:
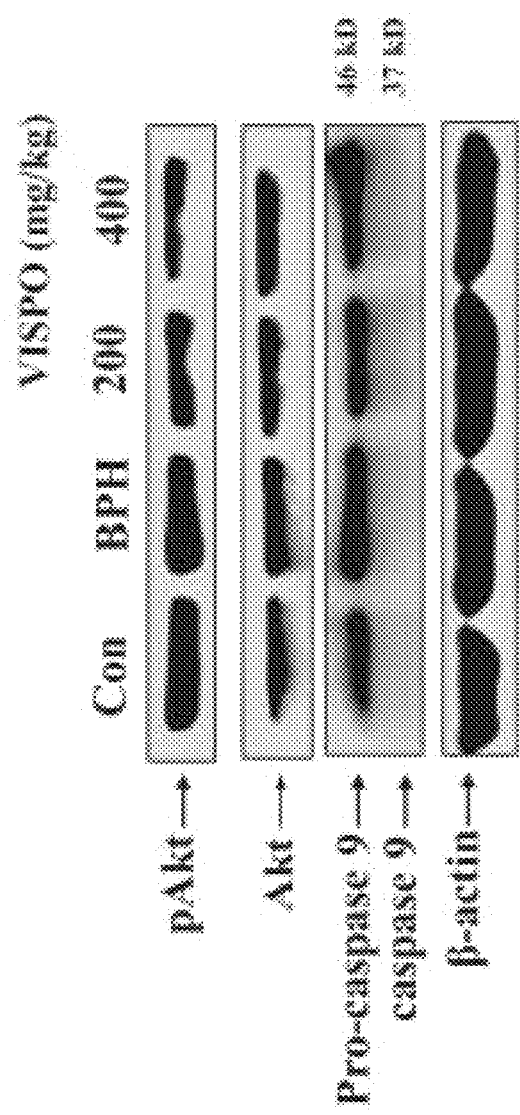
FIGS. 5A and 5B show the effect of an embodiment of the inventive composition on the expression of phosphorylated Akt and caspase-9 proteins in prostate tissue.
Figure 5B:
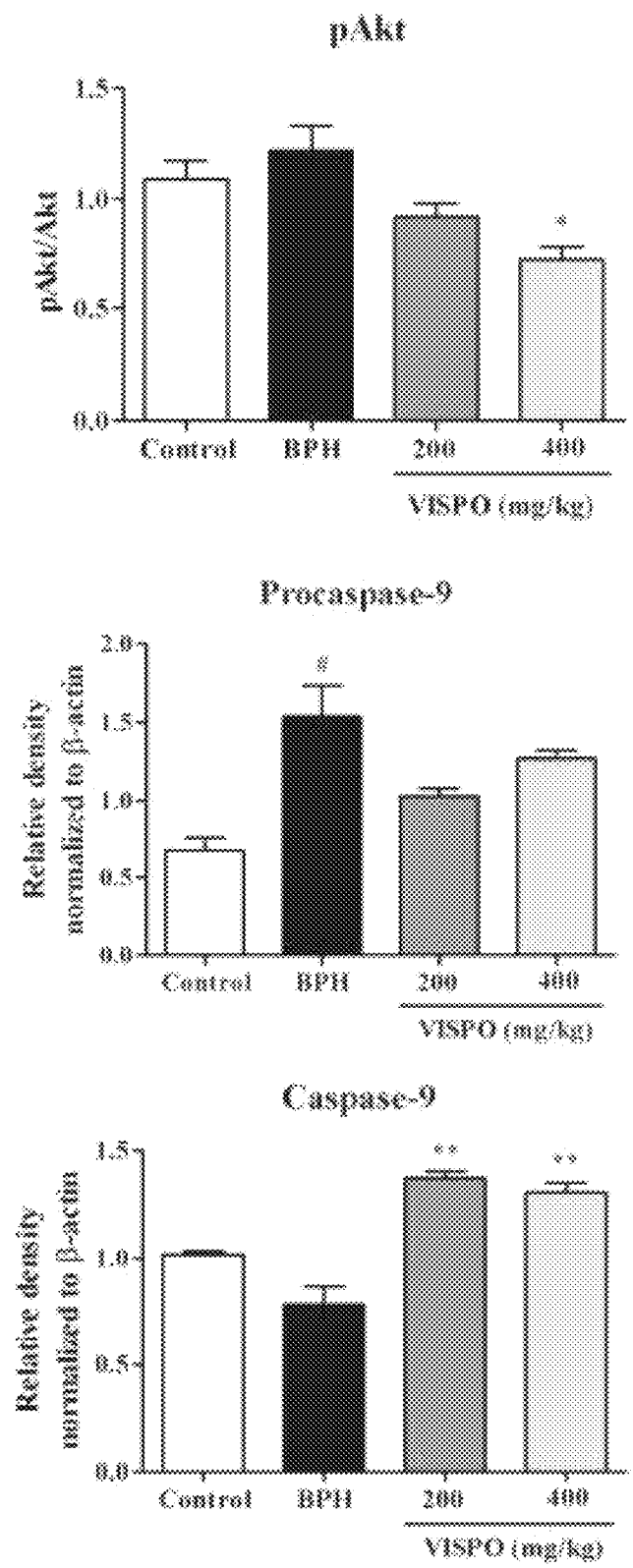
Figure 6A:
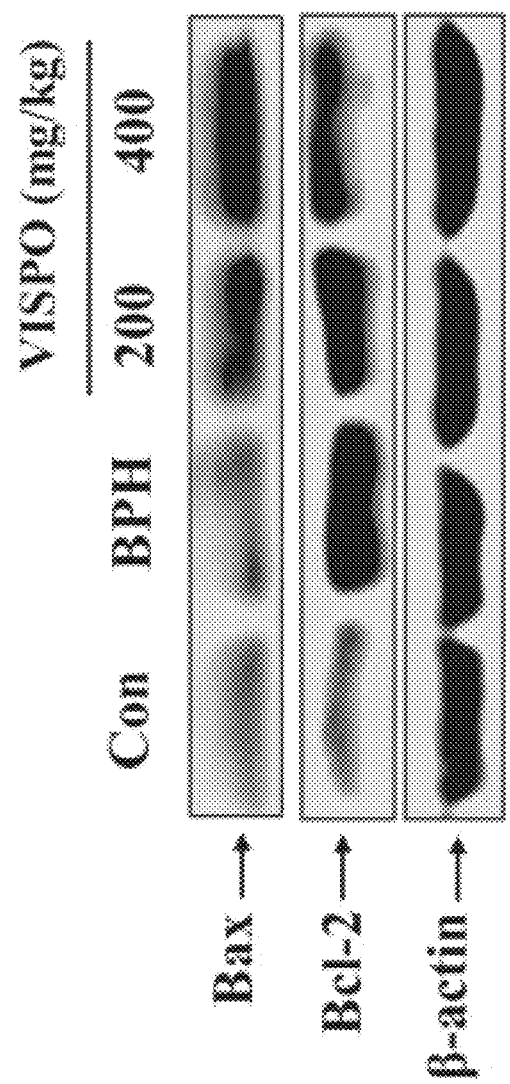
FIGS. 6A and 6B show the effect of an embodiment of the inventive composition on the expression of Bcl-2 family in prostate tissue.
Figure 6B:
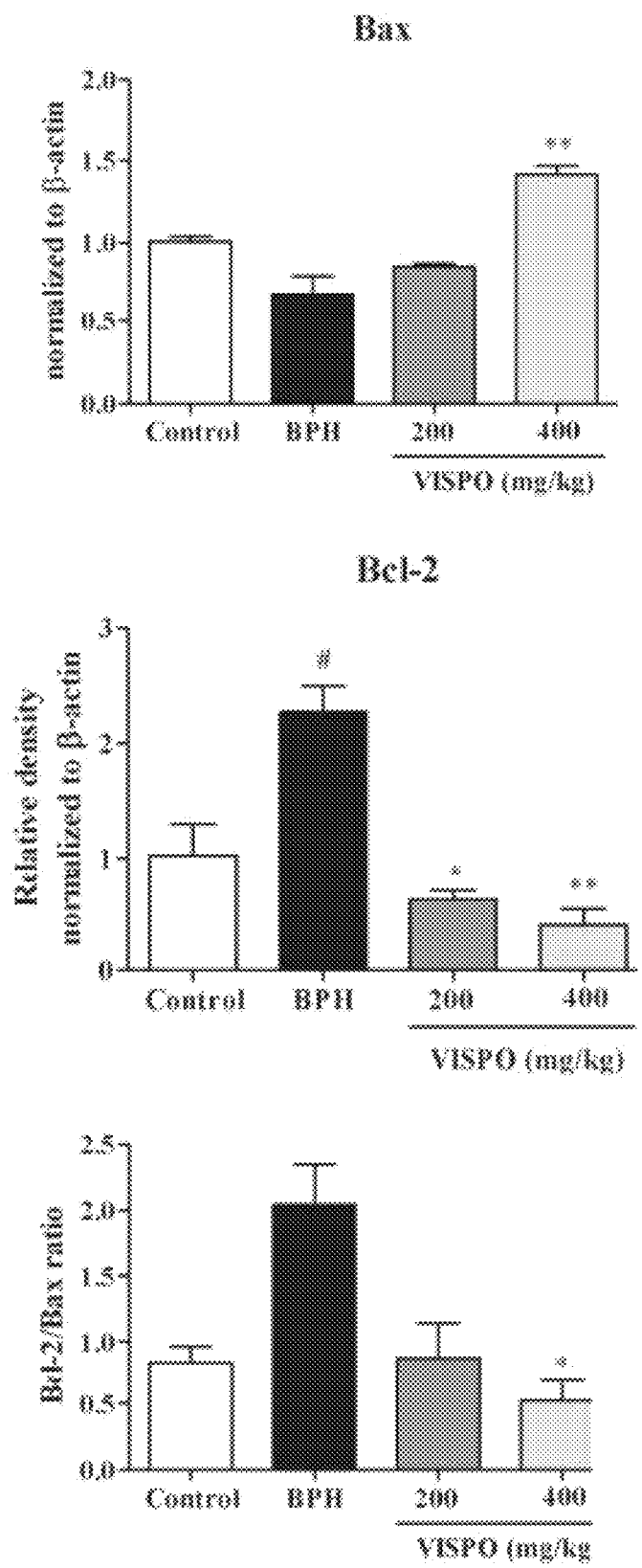

In the prostate tissue of BPH rats, there was increased phosphorylation of Akt at Ser-473. VISPO treatment effectively down-regulated the pAkt levels. There was a considerable decrease in the procaspase-9 level in the prostate tissue of BPH rats after treatment with respective doses of VISPO-β (FIGS. 5A and 5B). Further, VISPO treated groups showed a significant decrease in the antiapoptotic protein Bcl-2, but increased expression of proapoptotic Bax as compared to BPH group (p<0.01) (FIGS. 6A and 6B).

Example 7

Binding of β-Sitosterol with IkB and NF-kB Proteins

Molecular docking is the study of the interaction of ligands with target macromolecules. The three-dimensional crystal structures of IkB (PDB ID: 1IKN) and NF-kB (1NFI) were retrieved from the Protein Data Bank (http://www.rcsb.org/). AutoDock tool was utilized to generate grids, calculate dock score and evaluate the conformers of β-sitosterol bound in the active sites of target proteins. AutoDock 4.2 was employed to get docking and binding scores; which is implemented by Lamarckian genetic algorithm method. The ligand molecule was designed and the structure was analyzed using ACD/Chemsketch. The PRODRG server was used to minimize energy of drug compounds and 3D coordinates were prepared. A grid box was generated using AutoGrid to define docking spaces for the respective proteins. The Lamarckian genetic algorithm and the pseudo-Solis and Wets methods were applied for minimization, using default parameters (Rodriguez and Infante, 2011). The lowest binding energy and the inhibitory constant for each protein were obtained from the docking log files (Dlg).

Figure 7A:
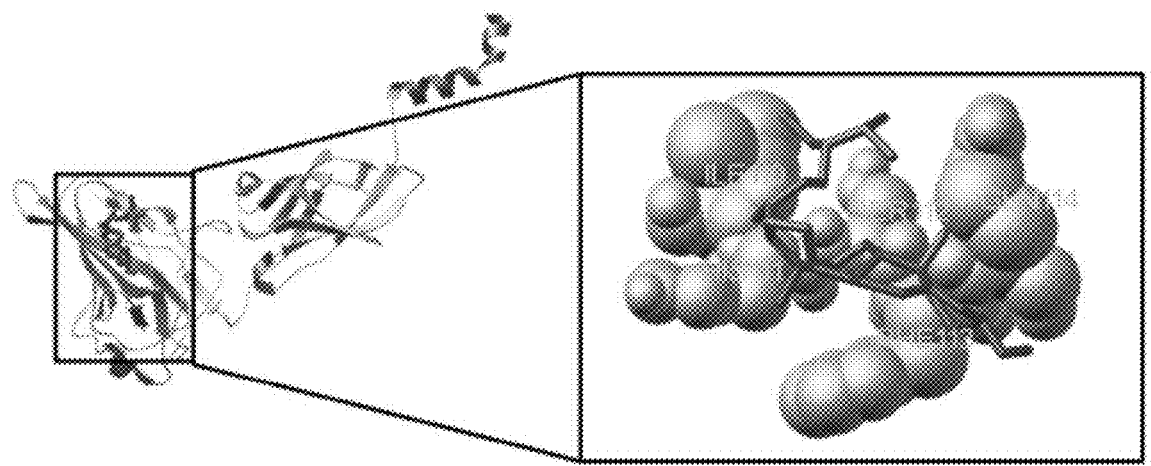
FIGS. 7A and 7B show the lowest energy binding poses of β-sitosterol with IkB and NF-kB proteins.
Figure 7B:
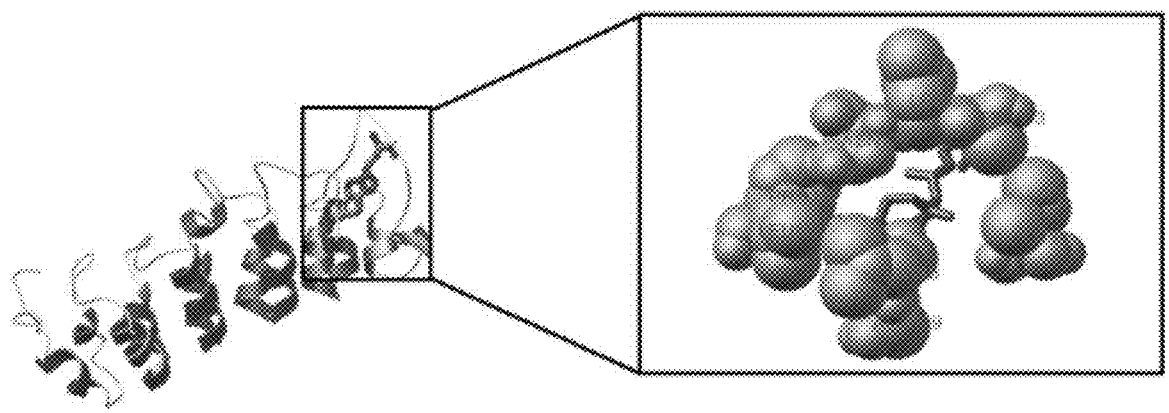
Figure 8C:
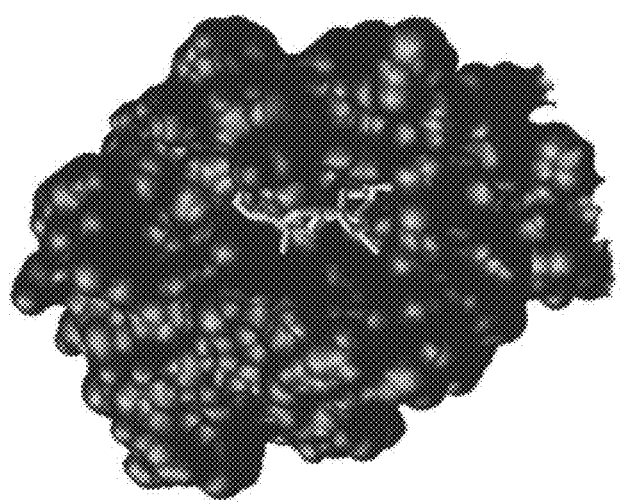
FIGS. 8A-8C show a representation of molecular interactions between β-sitosterol and the BH-3 binding groove of Bcl-2.
Figure 8B:
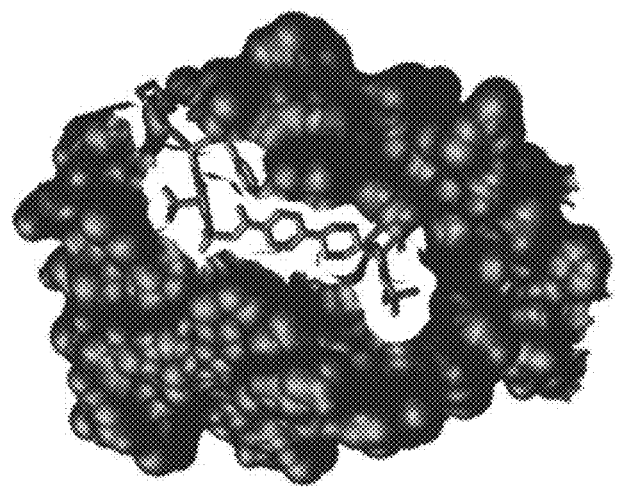
Figure 8A:
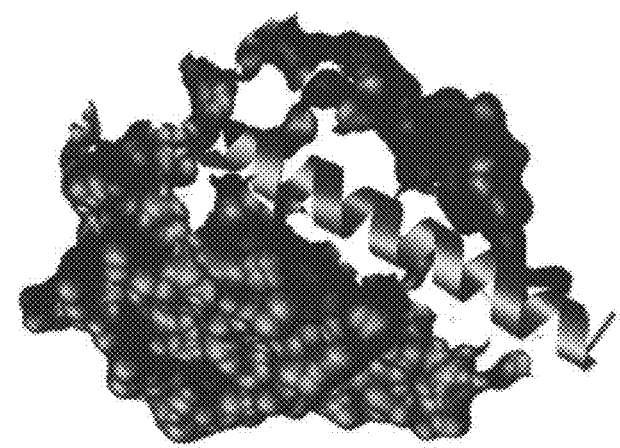

NF-kB is a transcriptional factor responsible for activation of inflammatory genes such as COX-2 and iNOS. However, under normal conditions in the cell, NF-kB remains in inactive form, bound to specific inhibitor IkB. From the western blot analysis of prostate tissue lysates, it became apparent that VISPO treatment down-regulated the NF-kB. The higher content of β-sitosterol in VISPO can prevent the dissociation of IkB from the IkB-NF-kB complex leading to the maintenance of NF-kB in its idle form. Hence, a docking analyses of β-sitosterol with IkB and NF-Kb was performed. As shown in Table 3, β-sitosterol preferably bound to IkB with a binding energy of −9.17 kcal/mol, while the phytosterol had a lower affinity towards NF-kB (−8.7 kcal/mol). Further, β-sitosterol had more hydrophobic interactions with the binding site of IkB. The docking of β-sitosterol into the target proteins are shown in FIG. 7. The higher affinity of β-sitosterol with IkB can show that the molecule inhibits the phosphorylation and degradation of IkB keeping NF-kB in its inactive form.

TABLE 3

Molecular docking score of β-sitosterol to IkB and NF-kB proteins

| Protein | Binding energy kcal/mol | Inhibitory constant (nM) | H-bond | Hydrophobic interactions |
|---------|------------------------|--------------------------|--------|--------------------------|
| IkB     | −9.17                  | 190.27                   | Ala127 | Phe103, Leu104, Ile94, Pro114, Leu115, Leu130, Ala129 |
| NF-kB   | −8.7                   | 421.04                   | Asn115 | Ile110, Phe113           |

Example 8

Molecular Docking of β-Sitosterol with the BH-3 Binding Groove of Antiapoptotic Bcl-2 Protein The three-dimensional crystal structure of Bcl-2 in complex with a Bax BH-3 peptide (PDB ID: 2XA0) and co-crystal structure of Bcl-2 and Navitoclax (PDB ID: 4LVT) were retrieved from Protein Data Bank. Further docking analysis of β-sitosterol was performed as mentioned in Example 7.

Figure 9A:
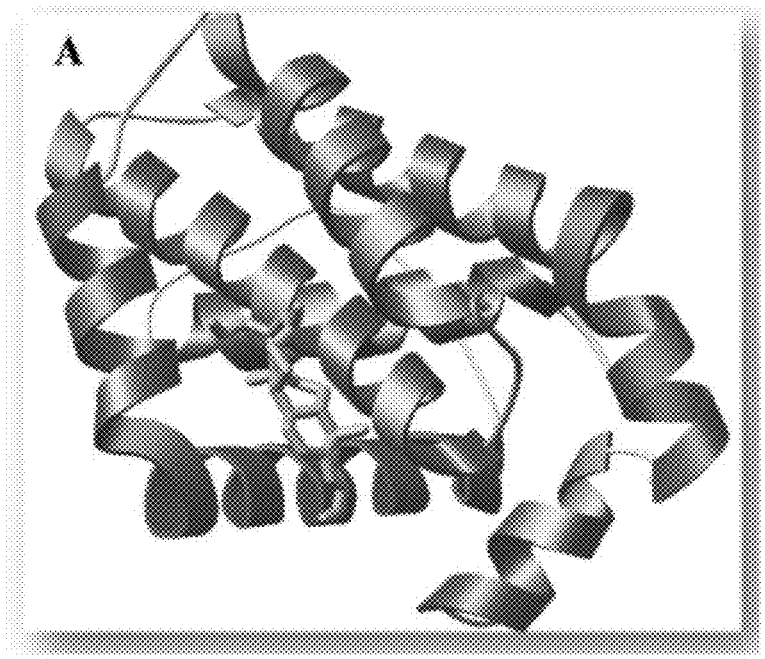
FIGS. 9A and 9B show hydrophobic interactions between β-sitosterol and the BH-3 binding groove of Bcl-2.
Figure 9B:
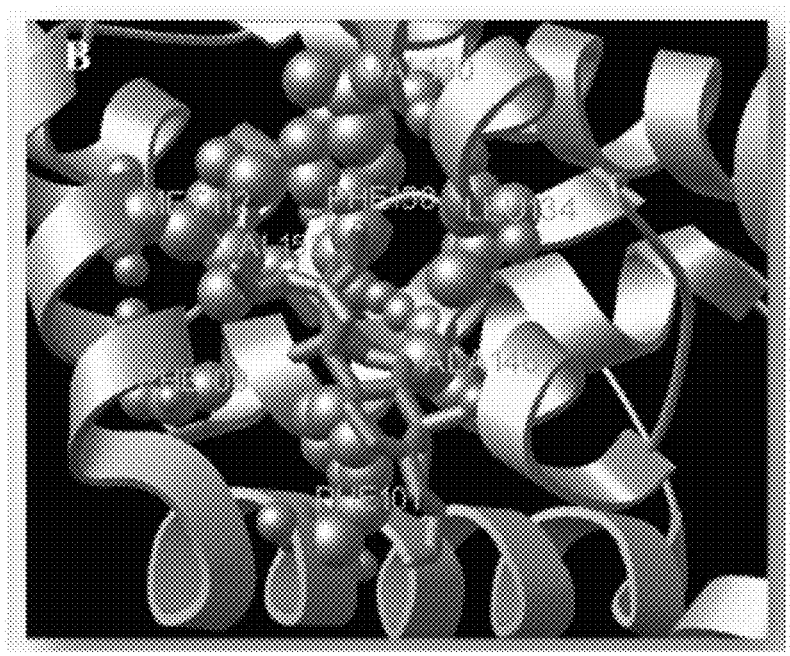
Figure 10:
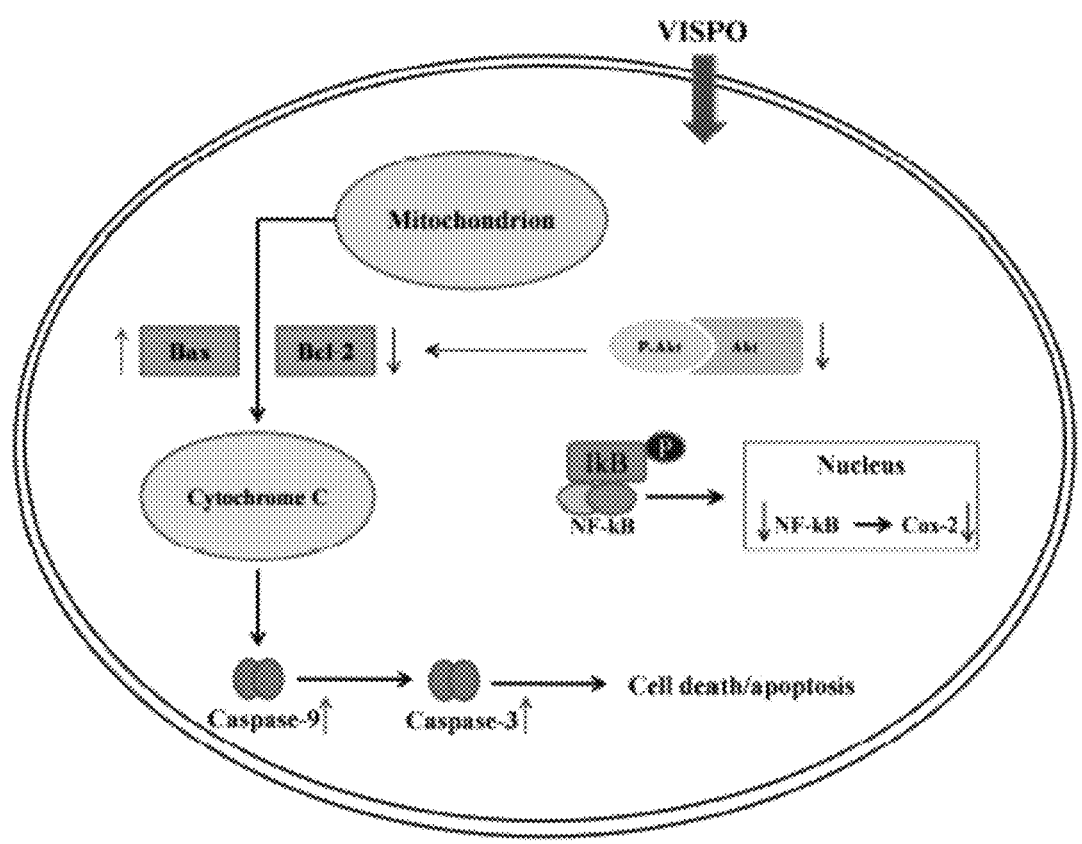
FIG. 10 is a schematic representation of the potential mechanism for the efficacy of an embodiment of the inventive composition in treating BPH.

In silico docking study was performed on the BH-3 binding groove of Bcl-2 protein in order to show the mechanism by which VISPO can induce apoptosis. The active principle β-sitosterol was made to dock to the co-crystal structure of Bcl-2 with its selective inhibitor, Navitoclax. The detailed molecular interaction of β-sitosterol and hydrophobic residues of BH-3 binding groove of Bcl-2 is shown in FIG. 9A. β-sitosterol interacted with hydrophobic enclosure of Phe101, Phe109, Met112, Val130, Leu134, Ala146, Phe150 and Val153 (FIG. 9B). The lowest binding energy was −8.79 kcal/mol.

INDUSTRIAL APPLICABILITY

As evident from the experimental data described herein, a composition of saw palmetto (*S. repens*) oil having 3% β-sitosterol has high efficacy, compared to conventional saw palmetto oil, in the treatment of benign prostate hyperplasia and associated inflammatory response.

The foregoing description, examples and accompanying drawings are intended to describe some, but not necessarily all, examples or embodiments of the invention. The described and exemplified embodiments are to be considered in all respects only as illustrative and not restrictive.

The contents of the detailed description, examples and accompanying drawings do not limit the scope of the invention in any way.

REFERENCES

1. Chughtai B, Lee R, Te A, Kalpan S. Role of inflammation in benign prostatic hyperplasia. Reviews in Urology 2011; 13(3): 147-150.
2. Gupta K, Yezdani M, Sotelo T, Aragon-Ching J B. A Synopsis of drugs currently in preclinical and early clinical development for the treatment of benign prostatic hyperplasia. Expert opin investing drugs. 2015; 24: 1059-1073.
3. Latil A, Petrissans M T, Roquet J, Robert G, de la Taille A. Effects of hexanic extract of *Serenoa repens* (Permixon® 160 mg) on inflammation biomarkers in the treatment of lower urinary tract symptoms related to benign prostatic hyperplasia. Prostate. 2015; 75: 1857-1867.
4. Minutoli L, Altavilla D, Marini H, Rinaldi M, Irrera N, Pizzino G et al. Inhibitors of apoptosis proteins in experimental benign prostatic hyperplasia: effects of *Serenoa repens*, selenium and lycopene. Journal of Biomedical Science 2014; 21: 19.
5. Nickel J C, Gilling P, Tammela T L, Morrill B, Wilson T H, Rittmaster R S. Comparison of dutasteride and finasteride for treating benign prostatic hyperplasia the enlarged prostate international comparator study (EPICS). BJU International 2011; 108: 388-394.
6. Nyamai D W, Arika W M, Rachuonyo H O, Wambani J R, Ngugi M P. Herbal management of benign prostate hyperplasia. Journal of Cancer Science and Therapy 2016; 8(5): 130-134.
7. Paba S, Frau R, Godar S S, Devot P, Marrosu F, Bortolato M. Steroid 5-reductase as a novel therapeutic target for schizophrenia and other neuropsychiatric disorders. Current Pharmaceutical Design 2011; 17: 151-167.
8. Pawlicki B, Zielinski H, Dabrowski M. Role of apoptosis and chronic prostatitis in the pathogenesis of benign prostatic hyperplasia. Polski Merkuriusz Lekarski 2004; 17: 307-310.
9. Robert G, Descazeaud A, Nicolaiew N, Terry S, Sirab N, Vacherot F et al. Inflammation in benign prostatic hyperplasia: a 282 patients' immunohistochemical analysis. Prostate 2009; 69(16): 1774-80.
10. Rodriguez A, Infante D: Characterization in silico of flavonoids biosynthesis in Theobroma cacao L. Net Biol 2011, 1: 34-45.
11. Rodriguez-Berriguete G, Fraile B, de Bethencourt F R, Prieto-Folgado A, Bartolome N, Nunez C et al. Role of IAPB in prostate cancer progression: immunohistochemical study in normal and pathological (benign hyperplastic, prostatic intraepithelial neoplasia and cancer) human prostate. BMC Cancer 2010; 10: 18-10.
12. Timothy J W, Areef I, Gerold S, Roderick M D, Joseph L, Cynthia M. Saw palmetto extracts for treatment of benign prostatic hyperplasia. Jama 1998; 280(18): 1604-1609.
13. Wang W, Bergh A, Damber J E. Chronic inflammation in benign prostate hyperplasia is associated with focal upregulation of cyclooxygenase-2, Bcl-2, and cell proliferation in the glandular epithelium. Prostate 2004; 61(1): 60-72.

The invention claimed is:

1. A composition for promoting normal urinary function, comprising saw palmetto oil having about 3% w/w β-sitosterol, wherein said composition is capable of reducing serum testosterone in a person when administered at a dosage of about 400 mg/kg body weight.

2. The composition of claim 1, wherein said composition further comprises a carrier, excipient, or combination thereof.

3. The composition of claim 2, wherein at least one of said carrier and said excipient are artificial.

4. The composition of claim 2, wherein said excipient is selected from the group consisting of binders, fillers, flow aids, disintegrants, lubricants, stabilizers, surfactants, and combinations thereof.

5. The composition of claim 1, wherein said composition is formulated for oral administration.

6. The composition of claim 1, wherein said composition is a nutritional supplement, food supplement, or beverage.

7. The composition of claim 1, wherein said composition is capable of treating in a person one or more symptoms selected from frequent and/or urgent need to urinate, increased frequency of urination, difficulty starting urination, weak urine stream, urine stream that stops and starts, dribbling at the end of urination, involuntary urination, painful urination, inability to completely empty the bladder, urinary tract infection, inability to urinate, and blood in the urine.

8. The composition of claim 1, wherein said composition is capable of treating in a person one or more of an enlarged prostate, increased prostate weight, prostate inflammation, inhibited apoptosis of prostate tissue, and prostate growth.

9. The composition of claim 1, wherein said composition is capable of reducing or inhibiting prostate inflammation in a person.

10. The composition of claim 1, wherein said composition is capable of decreasing prostate weight in a person.

11. The composition of claim 1, wherein said composition is capable of inhibiting hyperplasia in a prostate of a person.

12. The composition of claim 1, wherein said composition is capable of increasing apoptosis of prostate tissue in a person.

* * * * *